(12) United States Patent
Mortara (10) Patent No.: US 9,913,614 B2
(45) Date of Patent: Mar. 13, 2018

(54) IMPEDANCE MEASUREMENT SYSTEM

(71) Applicant: Mortara Instrument, Inc., Milwaukee, WI (US)

(72) Inventor: David W. Mortara, Milwaukee, WI (US)

(73) Assignee: MORTARA INSTRUMENT, INC., Milwaukee, WI (US)

(*) Notice: Subject to any disclaimer, the term of this patent is extended or adjusted under 35 U.S.C. 154(b) by 392 days.

(21) Appl. No.: 14/812,836

(22) Filed: Jul. 29, 2015

(65) Prior Publication Data

US 2015/0327811 A1    Nov. 19, 2015

Related U.S. Application Data

(63) Continuation of application No. 13/784,399, filed on Mar. 4, 2013, now Pat. No. 9,113,805.

(51) Int. Cl.
*A61B 5/00*    (2006.01)
*A61B 5/0408*    (2006.01)
(Continued)

(52) U.S. Cl.
CPC .......... *A61B 5/6843* (2013.01); *A61B 5/0424* (2013.01); *A61B 5/04085* (2013.01); *A61B 5/0531* (2013.01)

(58) Field of Classification Search
None
See application file for complete search history.

(56) References Cited

U.S. PATENT DOCUMENTS

| 3,730,171 A | 5/1973 | Namon |
| 4,459,993 A | 7/1984 | Foreman |

(Continued)

FOREIGN PATENT DOCUMENTS

| FR | 2908973 | 5/2008 |
| WO | WO-2012/092303 | 7/2012 |
| WO | WO-2012/097872 | 7/2012 |

OTHER PUBLICATIONS

Almasi, John J. et al., Automated Measurement of Bioelectric Impedance at Very Low Frequencies, Computers and Biomedical Research, vol. 7, No. 5, Oct. 1974, 8 pages.

(Continued)

*Primary Examiner* — Melissa Koval
*Assistant Examiner* — Felicia Farrow
(74) *Attorney, Agent, or Firm* — Foley & Lardner LLP (57) ABSTRACT

Systems and methods for monitoring the condition of electrodes used in biological signal measurement are provided. One method includes applying a first test signal having a first frequency to at least one of a plurality of electrodes and applying a second test signal having a second frequency to at least one of the plurality of electrodes. Both frequencies are below a frequency range associated with the biological signal. The method further includes capturing the biological signal while applying the plurality of test signals and generating an output signal that includes both the measured biological signal and the plurality of test signals. The method further includes retrieving an output amplitude for each of the plurality of test signals from the output signal and calculating an estimated impedance for each of the plurality of electrodes based on the retrieved output amplitudes of the plurality of test signals.

20 Claims, 3 Drawing Sheets

(51) Int. Cl.
*A61B 5/053* (2006.01)
*A61B 5/0424* (2006.01)

(56) References Cited

U.S. PATENT DOCUMENTS

| | | | |
|---|---|---|---|
| 4,610,254 | A | 9/1986 | Morgan et al. |
| 4,870,341 | A | 9/1989 | Pihl et al. |
| 4,919,145 | A | 4/1990 | Marriott |
| 5,025,784 | A | 6/1991 | Shao et al. |
| 5,184,616 | A | 2/1993 | Weiss |
| 5,282,840 | A | 2/1994 | Hudrlik |
| 5,300,093 | A | 4/1994 | Koestner et al. |
| 5,309,917 | A | 5/1994 | Wang et al. |
| 5,381,804 | A | 1/1995 | Shambroom |
| 5,649,969 | A | 7/1997 | Abrahamson et al. |
| 5,735,284 | A | 4/1998 | Tsoglin et al. |
| 5,819,741 | A | 10/1998 | Karlsson et al. |
| 5,879,308 | A | 3/1999 | Rasanen |
| 5,921,939 | A | 7/1999 | Danielsson et al. |
| 6,228,033 | B1 | 5/2001 | Koobi et al. |
| 6,339,722 | B1 | 1/2002 | Heethaar et al. |
| 6,487,449 | B1 | 11/2002 | Kaiser et al. |
| 6,493,576 | B1 | 12/2002 | Dankwart-Eder |
| 7,020,513 | B2 | 3/2006 | Faisandier |
| 7,161,362 | B2 | 1/2007 | Shambroom et al. |
| 7,622,988 | B2 | 11/2009 | Denison et al. |
| 7,684,856 | B2 | 3/2010 | Virtanen et al. |
| 7,783,345 | B2 | 8/2010 | Skrabal et al. |
| 7,848,795 | B2 | 12/2010 | Merilainen et al. |
| 8,068,905 | B2 | 11/2011 | Freeman et al. |
| 8,089,283 | B2 | 1/2012 | Kaplan et al. |
| 8,998,890 | B2 * | 4/2015 | Paul ................ A61N 1/40 600/547 |
| 2002/0046756 | A1 | 4/2002 | Laizzo et al. |
| 2006/0184060 | A1 | 8/2006 | Belalcazar et al. |
| 2010/0056880 | A1 | 3/2010 | Cho et al. |
| 2010/0100003 | A1 | 4/2010 | Chetham et al. |
| 2011/0046505 | A1 | 2/2011 | Cornish et al. |
| 2011/0208028 | A1 | 8/2011 | Rossi |
| 2011/0295096 | A1 | 12/2011 | Bibian et al. |
| 2012/0253206 | A1 | 10/2012 | Fukuda et al. |

OTHER PUBLICATIONS

Zepeda-Carapia, Israel et al., Measurement of Skin-Electrode Impedance for a 12-lead Electrocardiogram, Electrical and Electronics Engineering (ICEEE) (IEEE Cat. No. 05EX1097), 2nd International Conference on Electrical and Electronics Engineering (ICEEE), Sep. 7-9, 2005, 3 pages.

* cited by examiner

IMPEDANCE MEASUREMENT SYSTEM

CROSS-REFERENCE TO RELATED APPLICATIONS

This application is a continuation of U.S. application Ser. No. 13/784,399, filed Mar. 4, 2013, which is hereby incorporated by reference herein in its entirety.

BACKGROUND

The present disclosure relates generally to the field of biological signal measurement. More particularly, the present disclosure relates to systems of and methods for measuring impedance associated with electrodes used in measuring biological signals.

Long term monitoring of biological signals, such as electrocardiogram (ECG) signals, presents unique challenges in maintenance of signal quality. The quality of the electrode contact with a patient can and often does deteriorate over time. For example, a gel or other conductive substance used to effect electrical contact to the patient can dry out, causing the conductive properties to be affected. When the quality of the electrode contact deteriorates, the reliability/accuracy of the biological signal measurement is diminished. There is a need for a system for monitoring the quality of electrode contact that allows for continued monitoring after placement of electrodes without interfering with measurement of the biological signal.

SUMMARY

One embodiment of the disclosure relates to a method of monitoring a condition of a plurality of electrodes used in the measurement of a biological signal. The method includes applying a plurality of test signals to the plurality of electrodes. Applying the plurality of test signals to the plurality of electrodes includes applying a first test signal having a first frequency to at least one of the plurality of electrodes and applying a second test signal having a second frequency to at least one of the plurality of electrodes. The first frequency may be the same or different from the second frequency. Both the first frequency and the second frequency are below a frequency range associated with the biological signal. The method further includes capturing the biological signal while applying the plurality of test signals and generating an output signal that includes both the measured biological signal and the plurality of test signals. In some embodiments, the method may further include retrieving an output amplitude for each of the plurality of test signals from the output signal and calculating an estimated impedance for each of the plurality of electrodes based on the retrieved output amplitudes of the plurality of test signals.

Another embodiment relates to a system for monitoring a condition of a plurality of electrodes used in the measurement of a biological signal. The system includes a circuit configured to apply a plurality of test signals to the plurality of electrodes. The circuit is configured to apply a first test signal having a first frequency to at least one of the plurality of electrodes and apply a second test signal having a second frequency to at least one of the plurality of electrodes. The first frequency may be the same or different from the second frequency. Both the first frequency and the second frequency are below a frequency range associated with the biological signal. The circuit is further configured to capture the biological signal while applying the plurality of test signals and generate an output signal that includes both the measured biological signal and the plurality of test signals. In some embodiments, the method may be further configured to retrieve an output amplitude for each of the plurality of test signals from the output signal and calculate an estimated impedance for each of the plurality of electrodes based on the retrieved output amplitudes of the plurality of test signals.

Another embodiment relates to a system for measuring an electrocardiogram (ECG) signal. The system includes a plurality of electrodes and a circuit including a microprocessor and a DC amplifier. The circuit is configured to apply a plurality of test signals to the plurality of electrodes. The circuit is configured to apply a first test signal having a first frequency to at least one of the plurality of electrodes and apply a second test signal having a second frequency to at least one of the plurality of electrodes. The first frequency may be the same or different from the second frequency. Both the first frequency and the second frequency are less than 0.5 Hz and are below a frequency range associated with the ECG signal. The circuit is further configured to capture the ECG signal while applying the plurality of test signals and generate, using the DC amplifier, an output signal that includes both the measured ECG signal and the plurality of test signals. The circuit is further configured to retrieve an output amplitude for each of the plurality of test signals from the output signal and to calculate an estimated impedance for each of the plurality of electrodes based on the retrieved output amplitudes of the plurality of test signals. The system further includes a display device configured to display a visual representation of the ECG signal and to display a quantitative indication of a condition of the plurality of electrodes to the user. The quantitative indication is based on the calculated impedances for the plurality of electrodes.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Referring generally to the figures, systems and methods that may be used to monitor the impedance of electrodes used in measuring biological signals (e.g., electrocardiogram (ECG) signals, electroencephalogram (EEG) signals, etc.) are provided according to exemplary embodiments. Electrode contact quality may deteriorate over time after the electrodes have been applied to a patient, resulting in diminishing accuracy of the measured biological signals. From time to time, electrodes may need to be repositioned or replaced to ensure the accuracy of the measured signals.

Some systems are configured to test the contact impedance of the electrodes at the time of application of the electrodes. While this may help ensure that the initial contact between the electrodes and the patient is good, application-time measurement does not reliably forecast the long term condition of electrode contact quality.

Some systems are configured to monitor the electrodes after application by applying test signals used to measure the impedance associated with the electrodes. Such systems may utilize test signals that interfere with the measurement of the biological signal and require that monitoring of the biological signal be interrupted to test the electrode impedance. Interruption of monitoring of the biological signal is undesirable. Manually interrupting monitoring of the biological signal imposes burdens on health care providers, particularly since the time interval to deterioration of electrode contact quality (e.g., unacceptable increased electrode impedance) may not be readily predicted. Automatically interrupting monitoring of the biological signal presents risks that important events, such as those that are the purpose of the monitoring, may be missed while the electrodes are being tested.

The systems and methods of the present disclosure allow for testing the impedance of multiple electrodes concurrent with measuring the biological signal without interfering with the biological signal measurement (e.g., such that, during at least part of the time in which the biological signal is being measured, one or more of the electrodes are also being tested). Multiple test signals may be applied to the electrodes being tested. A first test signal may be applied to at least one electrode, and a second test signal may be applied to at least one other electrode. A frequency of the test signals may be below a frequency range associated with the biological signal being measured. At least a portion of the biological signal may be captured while one or more of the test signals are being applied, and an output signal may be generated that includes both the test signals (e.g., lower-frequency components of the output signal) and the measured biological signal (e.g., higher-frequency components of the output signal). The output amplitude for each of the test signals may be retrieved, and an estimated impedance for each of the electrodes may be calculated based on the output amplitudes. In some embodiments, the first test signal may have a first frequency (e.g., 0.05 Hz) and the second test signal may have a second frequency (e.g., 0.025 Hz) that is different from the first frequency. In some such embodiments, the test signals may be applied simultaneously, and the output from the test signals may be recovered based on the different frequencies of the test signals. In some embodiments, the first and second test signals may have the same frequency and may be applied at different times (e.g., consecutively). In some embodiments, a quantitative indication (e.g., impedance value, percentage of initial value, or other quantitative indicator) of the condition of the electrodes may be generated based on the estimated impedances and may be provided to the user (e.g., on a display). In some embodiments, the estimated impedances may be compared to a threshold impedance, and an alert may be generated indicating to the user that there is a problem with one of the electrodes when the estimated impedance exceeds the threshold value.

Figure 1:
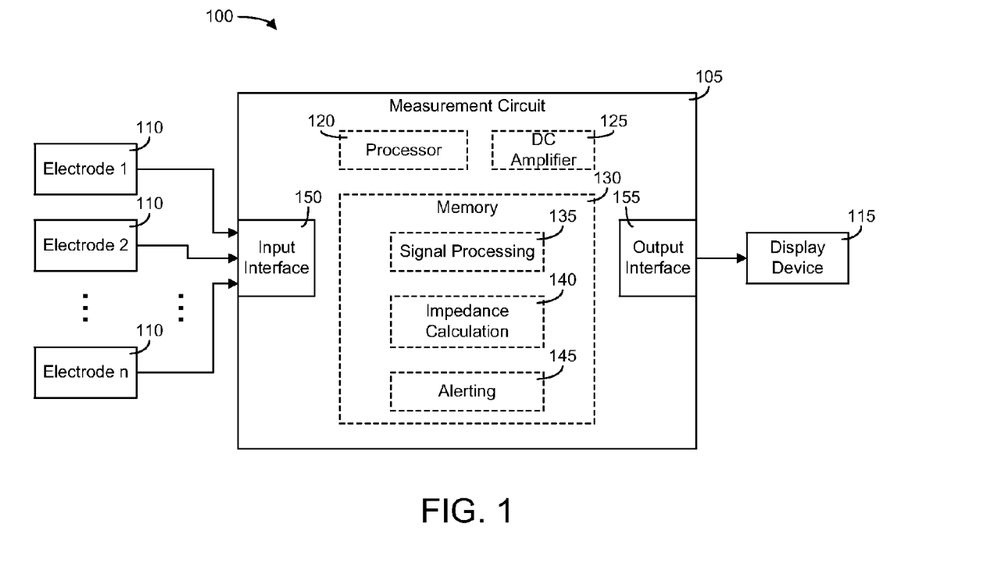
FIG. 1 is a block diagram of a system for monitoring the condition of one or more electrodes used in measuring a biological signal according to an exemplary embodiment.

Referring now to FIG. 1, a system 100 that may be used to measure a biological signal (e.g., ECG, EEG, etc.) of a patient is provided according to an exemplary embodiment. The biological signal may be measured by a measurement circuit 105 using two or more electrodes 110 connected to an input interface 150. Electrodes 110 may be placed at different locations on the body of the patient, such as at one or more locations on the chest, one or more locations on the limbs (e.g., arms and/or legs), one or more locations on the head, etc. The biological signal may be measured across two or more of electrodes 110. In some embodiments, the biological signal being measured may represent activity of the heart (e.g., ECG signals). In some embodiments, the biological signal being measured may represent brain activity (e.g., EEG signals).

Measurement circuit 105 is configured to monitor the quality of the electrode contact with a patient by measuring an impedance associated with each of electrodes 110. Measurement circuit 105 is configured to apply test signals to electrodes 110 and, based on the output amplitudes associated with the test signals, estimate an impedance associated with each of the electrodes. Measurement circuit 105 is configured to allow application of the test signals and estimation of the electrode impedances while the biological signal is being measured (e.g., simultaneous with measurement of the biological signal) without interrupting measurement of the biological signal and without degrading the quality of the measured biological signal.

Measurement circuit 105 may be implemented using hardware (e.g., electronic circuitry), software (e.g., instructions stored on a computer or machine-readable medium that are executable by a processor), or a combination of hardware and software. In some implementations, measurement circuit 105 may include a processor 120 (e.g., any general purpose or special purpose processor) configured to execute instructions stored in a memory 130 (e.g., any computer or machine-readable storage medium configured to store instructions and/or other data). Memory 130 may include one or more modules configured to perform various functions of measurement circuit 105. For example, a signal processing module 135 may be configured to process one or more signals generated using measurement circuit 105 and/or electrodes 110 (e.g., to extract output test signals from a combined output signal). An impedance calculation module 140 may be configured to calculate impedance values associated with each of electrodes 110 based on the output signal components corresponding with the test signals. In some embodiments, an alerting module 145 may be configured to generate alerts when one or more electrodes 110 have an impedance that exceeds a threshold (e.g., indicating that the electrode may no longer be taking accurate measurements of the biological signal).

Figure 2:
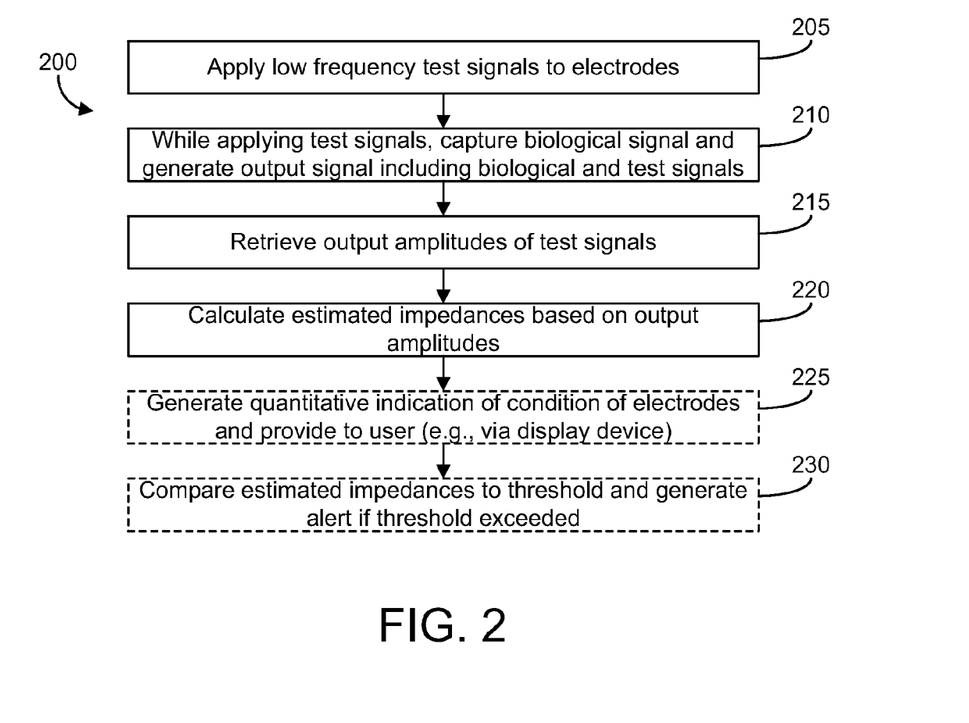
FIG. 2 is a flow diagram of a process for monitoring the condition of one or more electrodes according to an exemplary embodiment.

FIG. 2 illustrates a flowchart of a process 200 that may be used by system 100 (e.g., measurement circuit 105) to monitor the impedance of electrodes 110 according to an exemplary embodiment. Referring now to both FIGS. 1 and 2, circuit 105 may apply at least two test signals to electrodes 110 (205). The test signals include at least a first test signal having a first frequency and a second test signal having a second frequency. In some embodiments, the first frequency and the second frequency may be different frequencies (e.g., 0.025 Hz and 0.05 Hz). Such embodiments may allow system 100 to test multiple electrodes at the same time (e.g., within the same measurement window), and system 100 may recover the output associated with the test signals based on the different frequencies. In some embodiments, the first frequency and the second frequency may be substantially the same frequency. In such embodiments, the test signals may be applied at different times (e.g., consecutively), such that the output associated with the first signal may be recovered before the second signal is applied. Both the first frequency and the second frequency may be below (e.g., substantially below, such as at least an order of magnitude below) a frequency range associated with the biological signal. For example, for implementations in which the biological signal being measured is an ECG signal, the frequencies of the test signals may be below approximately 0.5 Hz (e.g., the minimum heart rate of the human heart). In some embodiments, the first test signal may have a frequency of approximately 0.025 Hz, and the second test signal may have a frequency of approximately 0.05 Hz. In some embodiments, both the first and second signals may have frequencies that are one or several orders of magnitude (e.g., 1000-fold) lower than a bandwidth or average frequency of the biological signal. The test signals may be applied over a measurement timeframe or window. For example, if a 0.025 Hz signal and a 0.05 Hz signal are applied, the measurement timeframe may be at least 40 seconds. In some implementations, the measurement timeframe may be at least 20 seconds. A relatively long measurement timeframe may help reduce the impact of noise on the measured signals.

Use of test signal frequencies below the frequency range of the biological signal allows the electrode impedance to be tested simultaneous with acquisition of the biological signal (e.g., such that at least part of the biological signal is measured while at least one test signal is being applied and/or measured) without interfering with and/or degrading the quality of the biological signal measurement. Some systems may utilize test signal frequencies above the bandwidth of the biological signal (e.g., for ECG signals, above an upper ECG bandwidth level, such as 150 Hz). Such systems may be subject to certain drawbacks. For example, the skin-electrode interface has both capacitive and resistive components. A large capacitive component can effectively mask a large resistive component if the impedance is measured at a high frequency. Additionally, some aspects of the biological signal, such as electronic pacemaker pulses, are typically detected by their very high frequency components. A high frequency test signal may interfere with effective pacemaker pulse detection.

Some systems may utilize a test signal frequency within the bandwidth of the biological signal. Such systems may require that measurement of the biological signal be suspended in order to test the impedance of the electrodes and suffer drawbacks associated with suspending measurement of the biological signal as described above. Some such systems may utilize switching devices to switch between modes in which electrode testing is performed and modes in which biological signal acquisition is performed. Some systems may avoid suspension of measurement by utilizing test signals at a particular frequency within the bandwidth and filtering out the test signal frequencies from the output signal before generating the final measured biological signal. Because the test frequencies are within the bandwidth of the biological signal, a portion of the biological signal data is lost when the test frequencies are filtered out. The filtered portions that are lost may include important portions of the biological signal.

Measurement circuit 105 utilizes test signal frequencies that are below the frequency range of the biological signal. By using low frequencies, the test signals applied to electrodes 110 to measure the impedances of electrodes 110 do not interfere with high frequency signal components relating to the biological signal (e.g., pacemaker pulses) in one embodiment. Utilizing low test frequencies may also reduce or eliminate the possibility of capacitive masking of the resistive component of the electrode-skin connection. Simultaneous biological signal acquisition and electrode impedance testing may be conducted, and the test frequencies are below the bandwidth of the biological signal, so the output biological signal and test signals may be retrieved without degrading the quality of the measured biological signal. In some embodiments, measurement circuit 105 may not include switching devices used to transition between electrode impedance testing and biological signal acquisition modes as measurement circuit 105 is configured to perform impedance testing and biological signal acquisition simultaneously. In some embodiments, use of low frequency test signals may help reduce the impact of noise in the impedance measurements performed by measurement circuit 105. For example, an ECG signal having an approximately 150 Hz bandwidth may have an average noise level of around 15 µV. Noise is directly related to frequency. If the maximum frequency used by the test signals is 0.05 Hz, the noise associated with the test signals would be approximately 50 times less than the average noise level of the ECG signal, or approximately 0.3 µV.

In some embodiments, a neutral ground connection and two input electrodes may be used to measure the biological signal. Each of the input electrodes has its own associated impedance. In order to measure these impedances, two test signals may be used. The first test signal with the first frequency is applied to the first electrode, and the second test signal with the second frequency is applied to the second electrode. In some embodiments, orthogonal test signals may be used. For example, a test signal having a frequency of approximately 0.05 Hz may be applied to one input electrode, and a test signal having a frequency of approximately 0.025 Hz may be applied to the other input electrode. When applied over a measurement timeframe (e.g., 40 seconds), the 0.05 Hz and 0.025 Hz components of the single lead may reveal the individual electrode impedances.

In some embodiments, more than two input electrodes may be used, and one electrode may serve as a reference electrode. The reference electrode receives a first test signal having a first frequency (e.g., 0.025 Hz). The remaining input electrodes receive the second test signal having the second frequency (e.g., 0.05 Hz), and the impedances of these electrodes are determined from the component of the bipolar signal formed with each electrode and the reference electrode having the second frequency (e.g., 0.05 Hz). The impedance of the reference electrode may be determined from the first frequency (e.g., 0.025 Hz) components of any of the bipolar signals.

Measurement circuit 105 may be configured to capture the biological signal and generate an output signal including both the biological signal and the test signals (210). The biological signal may be captured while one or more of the test signals are being applied. The generated output signal may be a combined signal including signal components associated with the test signals and components associated with the biological signal. For example, if 0.025 Hz and 0.05 Hz test signals are applied and a biological signal being measured has a bandwidth of 1-150 Hz, the generated output signal may include at least a first signal component at a frequency of approximately 0.025 Hz corresponding to the first test signal, a second component at a frequency of approximately 0.05 Hz corresponding to the second test signal, and a third signal component in a frequency range of approximately 1-150 Hz corresponding to the captured biological signal. In some implementations, measurement circuit 105 may include a DC amplifier 125 and/or an analog-to-digital converter configured to generate the output signal.

Measurement circuit 105 may be configured to retrieve the output amplitudes of the test signals from the generated output signal (215). In some embodiments, measurement circuit 105 may retrieve the output amplitudes by filtering out the components of the output signal having frequencies corresponding to the test signals. For example, measurement circuit may apply a demodulation at the frequencies (e.g., 0.025/0.05 Hz) followed by a low pass filter to recover a voltage proportional to the impedance.

In some embodiments, processor 120 may be configured to determine the output amplitudes by performing signal analysis on the output signal (e.g., using signal processing module 135). For example, the amplitudes of the output signal corresponding to the test frequencies may be measured by calculating the first frequency (e.g., 0.025 Hz) and second frequency (e.g., 0.05 Hz) Fourier signal components (e.g., Fourier sine wave components) from a measurement window or timeframe of input data (e.g., 40 second window). The window may be aligned to start at a time of a zero amplitude test signal. In some embodiments, leakage (e.g., distortion of Fourier components) may be limited by applying windowing weights (e.g., Hamming coefficients) in the process of calculating the desired Fourier component. In some embodiments, a combination (e.g., average) of the resultant amplitudes may be used as the final amplitude to estimate the impedance for one or more electrodes in order to decrease the impact of any noise that may be present in the output signal (e.g., due to the biological signal). Experimental data shows that a 4 nanoampere amplitude sine wave current results in an impedance amplitude noise of approximately 20 kΩ for a single 40 second window measurement. In embodiments in which the first and second test signals utilize the same frequency, the amplitudes of the output signal corresponding to the test signals may be determined by measuring Fourier signal component associated with the single frequency and using a longer measurement window (e.g., such that the measurement window is long enough to measure a first output associated with the first signal and a later second output associated with the second signal).

Once the output amplitudes associated with the test signals have been determined, measurement circuit 105 may calculate the estimated impedances for each of electrodes 110 based on the amplitudes (e.g., using impedance calculation module 140) (220). For example, the output amplitudes may represent measured voltage levels of the components corresponding to the test signal frequencies, and the input current values associated with the test signals may be known by measurement circuit 105. Once the voltages and currents are known, the impedances associated with the electrode contacts can be determined.

In some embodiments, measurement circuit 105 may be configured to generate a quantitative indication of the condition of electrodes 110 and provide the quantitative indication to a user (e.g., via a display device 115 connected to an output interface 155 of circuit 105). The quantitative indication of the condition of electrodes 110 may be based on the estimated impedances for electrodes 110. In some implementations, the quantitative indication may be the impedance values of electrodes 110 themselves. In some embodiments, the quantitative indication may be an indication of the relative quality of the electrode connection, for example with reference to a reference value (e.g., impedance value) representing an electrode connection in good condition or with reference to an initial impedance value for the electrode connection measured at first application of the electrode. In some embodiments, the quantitative indication may be represented as a percentage, a numerical value, a color, or any other relative indicator of the quality of the electrode connection.

In some embodiments, measurement circuit 105 may be configured to compare the estimated impedances for electrodes 110 to one or more threshold impedance values and generate an alert if the estimated impedances exceed a threshold (e.g., using alerting module 145) (230). The threshold value or values may represent impedance levels above which electrodes 110 may no longer provide accurate measurements of the biological signal. In some embodiments, measurement circuit 105 may be configured to provide generated alerts on display device 115, and the alerts may indicate to the user that one or more electrodes 110 should be repositioned or replaced to ensure accurate measurements of the biological signal. In some embodiments, multiple threshold values may be used. For example, a first threshold value may be associated with a non-urgent warning suggesting that the user perform maintenance on the electrode before the quality degrades to an unacceptable level, and a second threshold value may be an urgent warning indicating that the quality has degraded to a level that measurements by the electrode are no longer sufficiently accurate. In some embodiments, measurement circuit 105 may take additional actions in response to a threshold being exceeded, such as disabling measurement of the biological signal until the user addresses a problem with an electrode.

Figure 3:
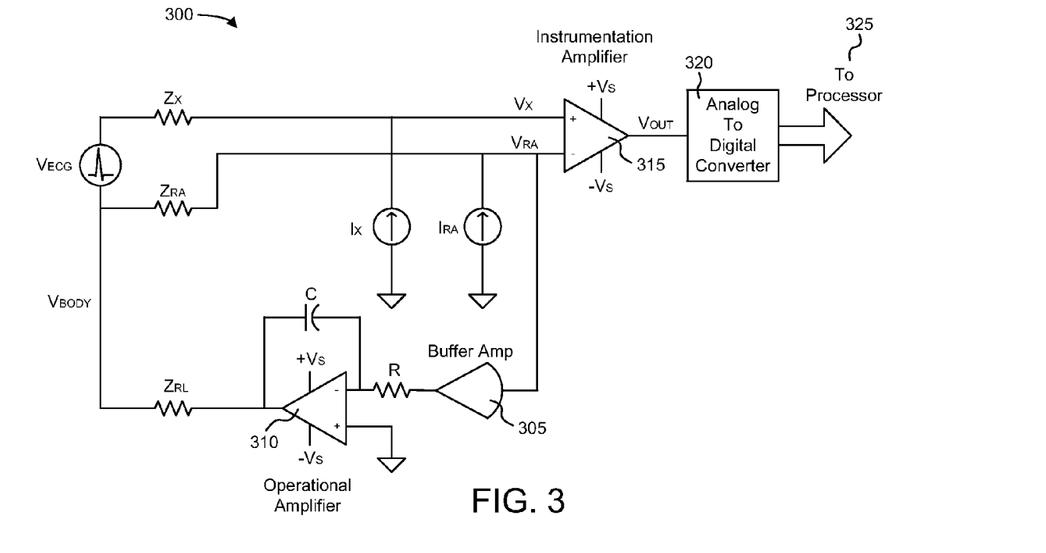
FIG. 3 is a circuit diagram of a measurement circuit according to an exemplary embodiment.

Referring now to FIG. 3, a circuit diagram of a measurement circuit 300 is shown according to an exemplary embodiment. Circuit 300 is one example implementation of measurement circuit 105 and may be configured to perform one or more functions described above with respect to circuit 105 and/or process 200.

Circuit 300 includes a buffer amplifier 305, an operational amplifier 310, an instrumentation amplifier 315, and an analog-to-digital converter (ADC) 320. An output of ADC 320 is sent to a processor 325 that is configured to process the output signal. Circuit 300 may represent a human body connected to a driven right leg ECG amplifier with impedance measurement ability.

Circuit 300 illustrates the following values:

$Z_X$=ECG Lead Impedance
$Z_{RA}$=Right Arm Lead Impedance
$Z_{RL}$=Right Leg Lead Impedance
$I_X$=Current Source for ECG Lead Impedance Measurement
$I_{RA}$=Current Source for Right Arm Lead Impedance Measurement
$V_{BODY}$=Voltage Due to Body
$V_{ECG}$=ECG Signal of Interest
$V_{ZRA}$=Voltage Due to RA Lead Impedance
$V_{ZX}$=Voltage Due to ECG Lead Impedance
$V_{OUT}$=Combined Output Voltage Signal The input impedance associated with instrumentation amplifier 315 and buffer amplifier 305 may be assumed to be greater than $Z_X$ and $Z_{RA}$. $V_{BODY}$ can be calculated as follows:

$$V_{BODY}=V_{RA}+I_{RA}*Z_{RA}$$

The control loop formed by the high gain integrator driving the right leg impedance forces the voltage $V_{RA}$ to be zero ($V_{RA}=0$). Accordingly, the equation for calculating $V_{BODY}$ can be modified to the following:

$$V_{BODY}=I_{RA}*Z_{RA}$$

$V_X$ can be calculated as follows:

$$V_X=V_{BODY}+V_{ECG}+I_X*Z_X=V_{ECG}+I_{RA}*Z_{RA}+I_X*Z_X$$

$V_{OUT}$ can be calculated as follows:

$$V_{OUT}=V_X-V_{RA}=V_{ECG}+I_{RA}*Z_{RA}+I_X*Z_X=V_{ECG}+V_{ZRA}+V_{ZX}$$

Two input signals having currents $I_X$ and $I_{RA}$ are applied to electrodes connected to circuit 300. The currents $I_X$ and $I_{RA}$ are modulated at two distinct frequencies (e.g., 0.05 Hz and 0.025 Hz). The amplitudes of the frequencies may be continuously recovered from the output signal, such as by using a cosine transform of a moving window of digital samples of $V_{OUT}$. The distinct frequencies allow for measurement of both $Z_X$ and $Z_{RA}$. In some embodiments, $Z_X$ may symbolically represent multiple electrodes, each with its own impedance, extending the concept reflected in this example to an arbitrary number of electrodes. The test signal driving frequencies are below the diagnostic portion of the biological signal and may be readily removed from $V_{OUT}$ to effect an output biological signal with no interference from the test signals. The test signal may have a very small amplitude without loss of efficacy because the average noise power measured over a relatively large measurement window (e.g., 20-40 seconds) (or noise density at the low test frequencies) is very low. The low amplitude test signals may have less potential for constraining dynamic range considerations and less potential for interfering with other instrumentation connected to the same source/body.

The disclosure is described above with reference to drawings. These drawings illustrate certain details of specific embodiments that implement the systems and methods of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, or by a special purpose computer processor incorporated for this or another purpose or by a hardwired system. No claim element herein is to be construed under the provisions of 35 U.S.C. § 112, sixth paragraph, unless the element is expressly recited using the phrase "means for." Furthermore, no element, component or method step in the present disclosure is intended to be dedicated to the public, regardless of whether the element, component or method step is explicitly recited in the claims.

Embodiments within the scope of the present disclosure include program products comprising machine-readable storage media for carrying or having machine-executable instructions or data structures stored thereon. Such machine-readable storage media can be any available media which can be accessed by a general purpose or special purpose computer or other machine with a processor. By way of example, such machine-readable storage media can include RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable storage media. Machine-executable instructions include, for example, instructions and data which cause a general purpose computer, special purpose computer, or special purpose processing machine to perform a certain function or group of functions. Machine or computer-readable storage media, as referenced herein, do not include transitory media (i.e., signals in space).

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM) or other non-transitory storage medium. The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing description of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

What is claimed is:

1. A method of monitoring a condition of a plurality of electrodes used in the measurement of a biological signal, the method comprising:

applying a first test signal having a first frequency to at least one of the plurality of electrodes and concurrently applying a second test signal having a second frequency different from the first frequency to at least one of the plurality of electrodes at a same time during which at least a portion of the first test signal is applied;

capturing the biological signal while applying the first and second test signals and generating an output signal that includes both the measured biological signal and the first and second test signals;

retrieving an output amplitude for each of the first and second test signals from the output signal;

calculating an estimated impedance for each of the plurality of electrodes based on the retrieved output amplitudes of the first and second test signals;

generating a quantitative indication of the condition of the plurality of electrodes based on the calculated estimated impedances for the plurality of electrodes; and providing the quantitative indication of the condition of the plurality of electrodes to a user.

2. The method of claim 1, wherein receiving an output amplitude for each of the first and second test signals comprises:

determining the output amplitude for the first test signal by measuring a first amplitude of a first signal component of the output signal corresponding to the first frequency; and determining the output amplitude for the second test signal by measuring a second amplitude of a second signal component of the output signal corresponding to the second frequency.

3. The method of claim 1, wherein the biological signal comprises an electrocardiogram (ECG) signal.

4. The method of claim 1, wherein the first frequency and the second frequency are both less than 0.5 Hz.

5. The method of claim 1, wherein calculating an estimated impedance for each of the plurality of electrodes comprises, for each electrode, calculating a plurality of estimated impedance values over a measurement timeframe, and wherein the method further comprises, for each electrode, calculating a final estimated impedance based on a combination of the plurality of estimated impedance values to reduce an impact of noise on the final estimated impedance.

6. The method of claim 1, further comprising, for each of the plurality of electrodes:

comparing the estimated impedance for the electrode with a threshold impedance; and generating an alert separate from the quantitative indication to the user indicating a problem with the electrode when the estimated impedance for the electrode exceeds the threshold impedance.

7. The method of claim 1, wherein the plurality of electrodes comprise two electrodes, and wherein applying the first and second test signals comprises applying the first test signal to a first electrode and applying the second test signal to a second electrode.

8. The method of claim 1, wherein the plurality of electrodes comprises at least three electrodes, wherein the at least three electrodes comprise a reference electrode and at least two remaining electrodes, and wherein applying the first and second test signals comprises applying the first test signal to the reference electrode and applying the second test signal to each of the at least two remaining electrodes.

9. A system for monitoring a condition of a plurality of electrodes used in the measurement of a biological signal, the system comprising:

a circuit configured to:

apply a first test signal having a first frequency to at least one of the plurality of electrodes and concurrently apply a second test signal having a second frequency different from the first frequency to at least one of the plurality of electrodes at a same time during which at least a portion of the first test signal is applied;

capture the biological signal while applying the first and second test signals and generate an output signal that includes both the measured biological signal and the first and second test signals;

retrieve an output amplitude for each of the first and second test signals from the output signal;

calculate, for each electrode, a plurality of estimated impedance values over a measurement timeframe based on the retrieved output amplitudes of the first and second test signals; and calculate, for each electrode, an estimated impedance based on a combination of the plurality of estimated impedance values for the electrode.

10. The system of claim 9, wherein the circuit is configured to retrieve the output amplitude for each of the first and second test signals by:

determining the output amplitude for the first test signal by measuring a first amplitude of a first signal component of the output signal corresponding to the first frequency; and determining the output amplitude for the second test signal by measuring a second amplitude of a second signal component of the output signal corresponding to the second frequency.

11. The system of claim 9, wherein the biological signal comprises an electrocardiogram (ECG) signal.

12. The system of claim 9, wherein the first frequency and the second frequency are both less than 0.5 Hz.

13. The system of claim 9, wherein the circuit is configured to:

generate a quantitative indication of the condition of the plurality of electrodes based on the calculated estimated impedances for the plurality of electrodes, the quantitative indication for each electrode comprising a value indicative of a relative quality of an electrode connection based on comparison of the calculated estimated impedance to at least one of:

an initial impedance value measured at application of the electrode; or a reference impedance value associated with a predetermined quality of the electrode connection; and provide the quantitative indication of the condition of the plurality of electrodes to a user.

14. The system of claim 13, wherein the circuit is configured to, for each of the plurality of electrodes:

compare the estimated impedance for the electrode with a threshold impedance; and generate an alert separate from the quantitative indication to the user indicating a problem with the electrode when the estimated impedance for the electrode exceeds the threshold impedance.

15. A system for measuring an electrocardiogram (ECG) signal, the system comprising:

a plurality of electrodes; and a circuit comprising a microprocessor and a DC amplifier, wherein the circuit is configured to:

apply a first test signal having a first frequency to at least one of the plurality of electrodes and concurrently apply a second test signal having a second frequency to at least one of the plurality of electrodes at a same time during which at least a portion of the first test signal is applied, wherein both the first frequency and the second frequency are below a frequency range associated with the ECG signal;

capture the ECG signal while applying the first and second test signals and generate, using the DC amplifier, an output signal that includes both the measured ECG signal and the first and second test signals;

retrieve an output amplitude for each of the first and second test signals from the output signal; and calculate an estimated impedance for each of the plurality of electrodes based on the retrieved output amplitudes of the first and second test signals.

16. The system of claim 15, wherein the circuit is configured to retrieve an output amplitude for each of the first and second test signals by:

determining the output amplitude for the first test signal by measuring a first amplitude of a first signal component of the output signal corresponding to the first frequency; and determining the output amplitude for the second test signal by measuring a second amplitude of a second signal component of the output signal corresponding to the second frequency.

17. The system of claim 15, wherein the circuit is configured to generate a quantitative indication of the condition of the plurality of electrodes based on the calculated impedances for the plurality of electrodes, the quantitative indication for each electrode comprising a value indicative of a relative quality of an electrode connection based on a comparison of the calculated estimated impedance to at least one of:

an initial impedance value measured at application of the electrode, or a reference impedance value associated with a predetermined quality of the electrode connection.

18. The system of claim 17, wherein the circuit is configured to:

compare the estimated impedance for the electrode with a threshold impedance;

generate an alert separate from the quantitative indication to a user indicating a problem with the electrode when the estimated impedance for the electrode exceeds the threshold impedance; and provide the quantitative indication of the condition of the plurality of electrodes and the alert to the user.

19. The system of claim 17, further comprising, a display device configured to:

display a visual representation of the ECG signal; and display the quantitative indication of the condition of the plurality of electrodes.

20. The system of claim 17, wherein the value comprises at least one of a numerical value or a percentage calculated based on the comparison of the calculated estimated impedance to the at least one of the initial impedance value or the reference impedance value.

* * * * *